United States Patent [19]

Wess et al.

[11] Patent Number: 4,938,232
[45] Date of Patent: Jul. 3, 1990

[54] COUPLING A MEMBRANE TO THE SKIN OF A HUMAN BEING

[75] Inventors: Othmar Wess, Munich; Reiner Groezinger, Alling; Kai Isdebski, Saulgau; Manfred Windsheimer, Germering; Wolfgang Erhardt, Fuerstenfeldbruck, all of Fed. Rep. of Germany

[73] Assignee: Dornier Medizintechnik GmbH, Friedrichshafen, Fed. Rep. of Germany

[21] Appl. No.: 426,494

[22] Filed: Oct. 23, 1989

Related U.S. Application Data

[63] Continuation of Ser. No. 942,259, Dec. 16, 1986, abandoned.

[30] Foreign Application Priority Data

Dec. 18, 1985 [DE] Fed. Rep. of Germany ....... 3544811

[51] Int. Cl.$^5$ ............................................... A61N 1/06
[52] U.S. Cl. ..................................... 128/802; 128/803
[58] Field of Search ............ 128/639, 640, 643, 24 A, 128/660.03, 783, 798, 802, 803; 156/235, 240, 349, 523, 574; 606/127, 128

[56] References Cited

U.S. PATENT DOCUMENTS

| | | | |
|---|---|---|---|
| 3,623,479 | 11/1971 | Day | 128/639 |
| 4,145,244 | 3/1979 | Covey | 156/240 X |
| 4,362,165 | 12/1982 | Carmon et al. | 128/640 |
| 4,637,399 | 1/1987 | Asai et al. | 128/642 X |
| 4,646,747 | 3/1987 | Lundback | 128/643 |

Primary Examiner—Ruth S. Smith
Attorney, Agent, or Firm—Ralf H. Siegemund

[57] ABSTRACT

A membrane is coupled to the skin of a human being, there being a gel layer provided between the membrane and the skin, the apparatus comprises a wiping structure movably mounted in a frame, one side of the membrane facing away from the skin and locally and progressively the membrane is forced against the gel layer and the skin so that progressively air bubbles in the gel layer are driven out of that layer and the layer is interposed bubblefree between the skin and the membrane. The wiper may swivel or roll; there may be plural wiper blades.

5 Claims, 1 Drawing Sheet

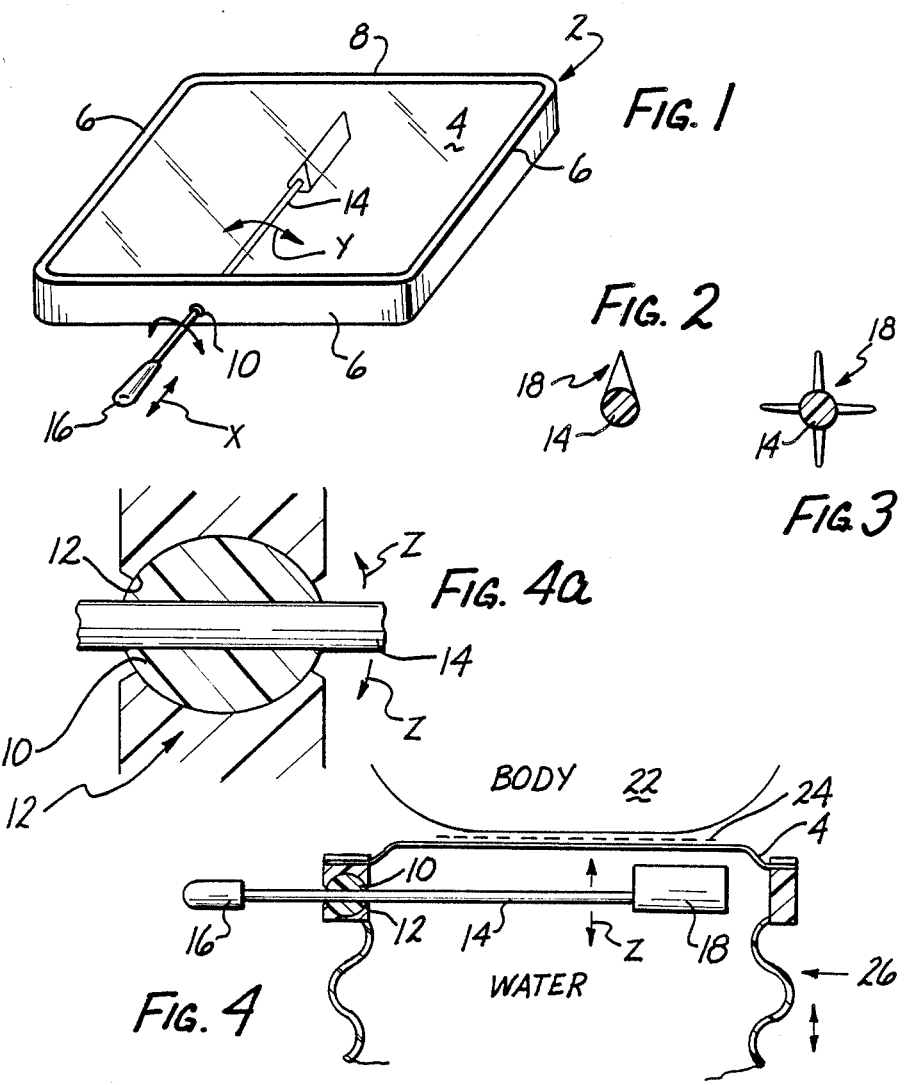
FIG. 1
FIG. 2
FIG. 3
FIG. 4a
FIG. 4
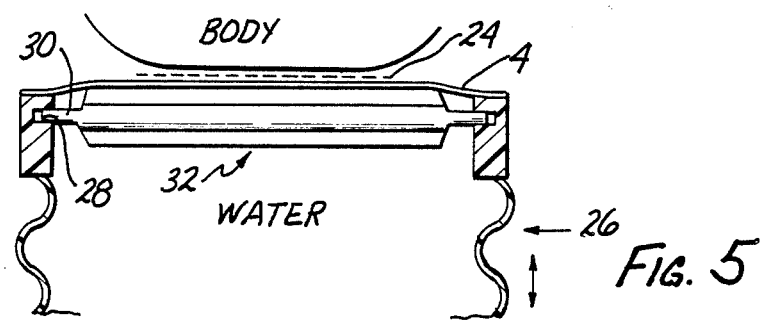
FIG. 5

COUPLING A MEMBRANE TO THE SKIN OF A HUMAN BEING

This is a continuation-in-part of co-pending application Ser. No. 06/942,259 filed on 12/16/1986 now abandoned.

BACKGROUND OF THE INVENTION

The present invention relates to coupling a membrane to the skin of a human being, for instance as a patient undergoing therapeutic or diagnostic treatment.

For purposes of medical diagnostic and/or therapeutic treatment, it has become more and more customary to use certain equipment by means of which radiation or waves such as shock waves or ultrasonic vibrations are coupled into the body of the patient without invasive surgery and without incurring any radiation energy losses or at least under and without conditions in which any losses are minimized.

As a first preparatory step for attaching a membrane to the skin, the body hair in the area in question is usually shaved off, and a gel layer is placed upon that bare skin. Now, the membrane of the medical treatment device or apparatus is forced against that gel layer. The purpose of this procedure is to provide an airfree and gapless coupling of the membrane to the skin, i.e. without inclusion or interposing of air bubbles. The membrane is in engagement and interfaces with the gel layer; the gel layer on the other hand is placed onto the skin directly and there should be no air bubbles anywhere. This being the desired state, it was found however that in practice bubbles are included, in the gel layer for example, through carelessness on part of the technician or nurse. These bubbles may be small but still their presence is highly detrimental and may in fact render questionable the success of the treatment i.e. the effect of the treatment may be diminished or even become ineffective entirely. Of course, medical technicians or physicians can acquire adequate manual skill and proficiency in the application of the gel layer such that indeed air bubbles are not included. This skill however is highly personal and simply cannot be expected as a matter of course.

It has, therefore, been suggested to evacuate the space between the skin of the patient on one hand and the membrane on the other hand, and to provide an immediate and direct contact between membrane and skin without, hopefully, intrusion of air bubbles. It was found in practice, however, that this bubblefree connection be guaranteed and is not even improveable through skillful handling. For these reasons therefor, one had to proceed in certain instances in a rather cumbersome fashion. For example, lithotripsy by means of shock waves such as the comminution of kidney stones has been practiced by placing the patient into a tub that is filled with water; the water is the coupling medium between the skin and the shock wave generator and focusing device, whereby however the water had to be carefully degassed. This procedure solves the problems of coupling the shock waves into the body of the patient, but it is obvious that placing the patient into a tub just for that purpose is a rather cumbersome way of proceeding. Still, this has been practiced in the past quite successfully but on the other hand it is apparent that there is room for improvement.

DESCRIPTION OF THE INVENTION

It is an object of the present invention to provide a new and improved device by means of which unskilled or semi-skilled personnel, for example, in a hospital, a clinic or the like, can prepare a patient by coupling the membrane of a treatment apparatus to the skin of the patient without the inclusion of air bubbles.

In accordance with the preferred embodiment of the present invention, it is suggested to attain the object by providing a membrane such that a movable and/or displaceable wiper is placed on one of its sides by means of which the membrane is locally pushed onto a gel layer that has been placed on the skin of the patient and facing the other side of the membrane, the wiper locally and progressively causes the membrane to be forced against the gel layer while any air bubble is so to speak, pushed out of the contact area. Therefore, an areal element will be provided with gel or adhesive, and the coupling process exposes the element (membrane) simultaneously to tension and compression, and this combination insures a good tight connection between the membrane, and the skin of the body of the patient.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

FIG. 1 illustrates a membrane held within a frame and presumed to be a part of a diagnostic or therapeutic piece of equipment, showing the inventive wiper in accordance with the preferred embodiment of the present invention for practicing the best mode thereof;

FIGS. 2 and 3 illustrates modification or details as far as a wiper in FIG. 1 is concerned;

FIG. 4 is a section view through the device membrane shown in FIG. 1; and

FIG. 5 is a view similarly to FIG. 4 but in a different embodiment of the invention.

Preceding now to the detailed description of the drawings, FIG. 1 illustrates a frame 2 being so to speak a window or the like for a therapeutic or diagnostic medical equipment and through which e.g. shock waves or ultrasonic waves may pass. The frame particularly is comprised of front bars or walls 6 and side walls 8. An elastic membrane 4 is clamped in between these walls and held taught by them. An articulated bearing 10 is provided in one of the walls being in this case, one of the side walls 8 which however is basically arbitrary and has to do primarily with questions of manual accessability under consideration of the physical dimensions of the equipment to which that membrane is connected whenever this particular frame 2 is made a part of diagnostic or therapeutic apparatus.

As shown in FIG. 4a bore 12 is provided with a socket configuration for a ball and socket bearing which includes further a ball-like element 10. A small rod 14 is slidably mounted within that ball for sliding along arrow X. Rod 14 can also be pivoted by means of the handle 16 in direction of arrow Y (FIG. 1) and arrow Z in FIGS. 4 and 4a. Thus, this particular bar or rod 14 is provided for axial and angular displacement, it can so to speak, be shifted into and out, from under the membrane 4 and wipe along its undersides. The rod 14 has an outer end that extends laterally from the frame and is provided with a handle 16 while a wiper blade 18, similar to a windshield wiper of a car or the like, is provided on the other end of rod 14. This wiper blade 18 may be provided just as a single wiper lip as shown in FIG. 2, or there maybe a plurality of such wipers 20 as shown in FIG. 3. Alternatively, the wiper may be provided by means of a fairly hard bristle.

FIG. 4 illustrates a section view of FIG. 1 shown in addition the skin 23 of the body 22 of a patient. In this case, one can see the membrane 4 as being more or less close to the skin 23 while a gel layer 24 is interposed. The frame 2 in this case is mounted at the end of bellows 26 for purposes of adjusting pressure as well as elevation of the membrane vis-a-vis some other equipment which is not shown. The interior 34 of the bellows 26 is for example, filled with water.

Another bellows 26' is shown in FIG. 5, the frame 2 there has indents or grooves 28, and pin ends 30 and 31 of a wiper rod 32 can roll in these grooves 28. The wiper may in this case be moved for example by means of a small motor or manually under utilization of a handle analogous to one shown in FIG. 4. In any event, the wiper is moved along the frame. The wiper blades are made of an elastic material. As the wiper is rotated and progressively wipes along the underside of the membrane and rolls along grooves 28, a gapless abutment of the membrane 4 obtains against the skin 23 of the body 22 of the patient. One or more of these roller kind of wipers may be moved from the center towards the frame end; also, it is possible that the lips or the wiper drum itself is made expandable or one can provide vibration in that the roller vibrates in some fashion for purposes of removing any air bubbles from the gel layer 24.

Generally speaking, any of the inventive devices is used as follows. The body 22 of the patient rest for example on a suitable support which is not shown, while the other equipment is stationary, and positioned adjacent to the skin 23 of the patient to which it is to be coupled. Now the rest is lowered so that the body 22 of the patient with the skin 23 comes into contact with the gel covered membrane 4. This membrane 4 on the other hand can be adjusted then or later by means of the bellows 26. The membrane in fact serves as a closure for an anterior space 34 which is filled with water. A shock wave generator and focusing device is provided at the other end of the bellows or some other piece of equipment for providing any kind of radiation or vibration is provided at that other lower end or the bottom. Some pressure i.e. some excessive pressure over the ambient atmospheric pressure is applied.

Now, by means of any of the wiper blades 18, through manual or motor driven wiper motion, the membrane is locally urged against the skin of the patient along a line and that local line of pressure application is moved outwardly as the wiper is swivelled or rolled from the center of the membrane towards the frame. In either case, air bubbles will be moved as the wiper progresses from the center to the outside and the bubbles are shifted so to speak, along and out of the area. Whether or not bubbles remain trapped somewhere in or along the periphery is inconsequential because the area in contact is not made critical in terms of dimensions and boundaries.

The invention is not limited to the embodiments described above, but all changes and modifications thereof, not constituting departures from the spirit and scope of the invention are intended to be included.

We claim:

1. An apparatus for use in coupling medical equipment to the skin of a human being, comprising a membrane said membrane being adapted to be connected to said medical equipment, a gel layer being provided on the membrane and adapted for interpositioning between the skin of the human being and the membrane, a movably mounted wiping structure disposed on a side of the membrane facing away from the side that is adapted to face the skin, the wiping structure being connected to a laterally displaced actuator; by means of said wiping structure the membrane is locally and progressively forced against the gel layer and thereby being adapted for forcing the gel layer against the skin so that upon movement of the wiping structure, progressively any air bubbles in the gel layer are driven out of that layer and the layer is interposed bubblefree between the skin and the membrane.

2. The apparatus as in claim 1, said membrane being held in a frame, the wiping structure including an articulated rod mounted in the frame, one end of the rod being accessible laterally from the outside and carrying on its other end a wiper device.

3. The apparatus as in claim 2 further including means for mounting the rod in the frame for pivoting of the rod and for axial shifting the rod relative to the frame.

4. The apparatus as in claim 1 wherein said wiping structure includes a shaft having a plurality of wiper blades.

5. The apparatus as in claim 1 further comprising a frame, said membrane being held in the frame, the wiping structure including a rotatable roller with a plurality of axially and radially extending wiper blades, said roller being mounted for rotation and rolling inside said frame.

* * * * *